US00PP27861P3

(12) United States Plant Patent
Misato

(10) Patent No.: US PP27,861 P3
(45) Date of Patent: Apr. 4, 2017

(54) ***SENECIO CRUENTUS* PLANT NAMED 'SUNSENEBUBAKAI'**

(50) Latin Name: ***Senecio cruentus* (Masson ex L'Hér.) DC.**
Varietal Denomination: Sunsenebubakai

(71) Applicant: SUNTORY FLOWERS LIMITED, Tokyo (JP)

(72) Inventor: Tomoya Misato, Omihachiman (JP)

(73) Assignee: SUNTORY FLOWERS LIMITED, Tokyo (JP)

( * ) Notice: Subject to any disclaimer, the term of this patent is extended or adjusted under 35 U.S.C. 154(b) by 194 days.

(21) Appl. No.: 14/121,584

(22) Filed: Sep. 19, 2014

(65) Prior Publication Data

US 2015/0208568 P1 Jul. 23, 2015

Related U.S. Application Data

(60) Provisional application No. 61/965,150, filed on Jan. 23, 2014.

(51) Int. Cl.
*A01H 5/02* (2006.01)

(52) U.S. Cl.
USPC ..... Plt./480

(58) Field of Classification Search
USPC ..... Plt./480
See application file for complete search history.

(56) References Cited

PUBLICATIONS

Registration No. 10653, Registration date Sep. 30, 2002, Suntory Flowers Company, 1 page.

*Primary Examiner* — Keith Robinson
(74) *Attorney, Agent, or Firm* — Kilpatrick Townsend & Stockton LLP

(57) ABSTRACT

Disclosed herein is a new and distinct variety of *Senecio* plant having blue and white-bicolored ray floerts, and upright and medium sized appearance.

2 Drawing Sheets

Botanical designation: *Senecio cruentus* (Masson ex L'Hér.) DC.

Cultivar denomination: 'Sunsenebubakai'.

BACKGROUND OF THE INVENTION

The present invention relates to a new and distinct variety of *Senecio* plant, which is hereinafter referred to as 'Sunsenebubakai'.

A *Senecio cruentus* (Masson ex L'Hér.) DC. is a very popular plant that is used in flower bedding and potting in the winter and spring seasons.

The purpose of this invention is to obtain a new *Senecio* cultivar with abundant and large sized petals having blue and white-bicolored ray floerts, and an upright and medium sized appearance.

The new *Senecio* plant originated from cross-pollination of the female parent '09-83' and the male parent '09-09'. The female parent '09-83' (unpatented) used in the crossing of 'Sunsenebubakai' is a strain of the applicant's breeding lines (i.e., proprietary *Senecio* selection), having white petals, and the male parent '09-09' (unpatented) used in the crossing of 'Sunsenebubakai' is a strain of the applicant's breeding lines (i.e., proprietary *Senecio* selection), having light blue and pink-bicolored petals. The cross-pollination was conducted in March, 2010, at Higashiomi, Shiga, Japan.

In February 2011, the seedlings obtained by the crossing were planted in a field, and some seedlings were selected in view of growth habit, flower size and color thereof. Shortly thereafter stem tip culturing was carried out, and then the propagation was started.

In November 2013, the cultivation of the seedlings was repeated. The botanical characteristics of that plant were then examined, using similar variety 'Sunsenebuba' for comparison. As a result, it was concluded that this *Senecio* plant is distinguishable from any other variety, whose existence is known, and has uniform and stable characteristics.

The new variety of *Senecio* plant was then named 'Sunsenebubakai'.

SUMMARY OF THE INVENTION

This new variety is unlike any *Senecio* commercially available as evidenced by the following unique combinations of characteristics.

1. Abundant and large sized petals having blue and white-bicolored ray floerts.
2. Upright and medium sized appearance.

The new variety 'Sunsenebubakai' differs from the similar variety 'Sunsenebuba', which was applied for Japanese plant variety protection (the application number: 12095; the application date: 199/11/10; the registration number 10653; the registration date: Sep. 31, 2002), in the following points.

1. The ray floret color of 'Sunsenebubakai' is bicolor, blue (95B) and white (NN155C). That of 'Sunsenebuba' is bicolor, violet-blue (93B) and white (NN155C).
2. The flower diameter of 'Sunsenebubakai' is about 81 mm. That of 'Sunsenebuba' is about 68 mm.
3. Ray floret length of 'Sunsenebubakai' is about 31 mm. That of 'Sunsenebuba' is about 27 mm.
4. The disc diameter of 'Sunsenebubakai' is about 16 mm. That of 'Sunsenebuba' is about 12 mm.

This new variety of *Senecio* plant 'Sunsenebubakai' was asexually reproduced by the use of cuttings at Higashiomi, Shiga, Japan, and homogeneity and stability thereof were confirmed. The instant plant retains its distinctive characteristics and produces true to type in successive generations.

BRIEF DESCRIPTION OF THE PHOTOGRAPHS

The depicted plants had been reproduced by the use of cuttings and were photographed during November 2013 while growing outdoors in wall pots which were about 15 cm in size at an age of approximately 6 months.

FIG. 1 is a photograph of a typical plant of the new variety of *Senecio* plant 'Sunsenebubakai' while growing in a pot.

FIG. 2 is a photograph of a close view of flowers of the new variety of *Senecio* plant 'Sunsenebubakai'.

DETAILED BOTANICAL DESCRIPTION

In November 2013, the cultivation of the seedlings was repeated at Higashiomi, Shiga, Japan. The average day temperature was about 10° C., and the average night temperature was about 5° C. The plants were grown under natural sunlight. The number of days to flowering (response time) was about 22 weeks. The quality was maintained for about 150 days. The plants had temperature resistance to about 0° C. (the lowest temperature) and about 30° C. (the highest temperature). Further, the plants had the same tolerance to pests and pathogens as a typical *Senecio* plant.

For the parentage information: The female parent '09-83' (unpatented) used in the crossing of 'Sunsenebubakai' is a strain of the applicant's breeding lines (i.e., proprietary selection of *Senecio cruentus*), having white petals, and the male parent '09-09' (unpatented) used in the crossing of 'Sunsenebubakai' is a strain of the applicant's breeding lines (i.e., proprietary selection of *Senecio cruentus*), having light blue and pink-bicolored petals.

For the propagation information: The number of days in which roots started to form during the summer was about 7 days; approximate soil and/or air temperature during the summer was around 18-20° C.; number of days in which roots started to form during the winter was about 7 days; approximate soil and/or air temperature during the winter was around 18-20° C.; number of days to produce a rooted young plant during the summer was about 28 days; number of days to produce a rooted young plant during the winter was about 28 days; root density was fine; root branching was free; root color was NN155B; and root texture was fibrous.

The botanical characteristics of the new and distinct variety of *Senecio* plant named 'Sunsenebubakai' at an age of approximately 6 months are shown in the following Table. In the following description, the color-coding is in accordance with The Horticultural Colour Chart of The Royal Horticultural Society, London, England (R.H.S. Colour Chart 5th edition 2007).

PLANT VARIETY DESCRIPTION

| CHARACTERISTIC | APPLICATION VARIETY Sunsenebubakai | |
|---|---|---|
| ANNUAL, BIENNIAL or PERENNIAL? | Grown as annual | |

-continued

PLANT VARIETY DESCRIPTION

| CHARACTERISTIC | APPLICATION VARIETY Sunsenebubakai | |
|---|---|---|
| TYPE OF PLANT: i.e., TREE, SHRUB, SUBSHRUB, VINE, CUT FLOWER, POTTED PLANT | Potted plant | |
| APPROPRIATE CONTAINERS +/or CROPPING SYSTEM | Ideal for pots | |
| GROWTH HABIT | Upright | |
| PLANT HEIGHT | About 47.0 | cm |
| PLANT DIAMETER OR AREA OF SPREAD | About 57.0 | cm |
| PLANT VIGOR | Vigorous | |
| BRANCHING HABIT | Freely branching | |
| PINCHING REQUIRED? | Not required, 1~2 pinching stimulate brunching | |
| NUMBER OF LATERAL BRANCHES | About 8 | |
| LATERAL BRANCH LENGTH | About 29.5 | cm |
| LATERAL BRANCH DIAMETER | About 7.1 | mm |
| INTERNODE LENGTH | About 15.7 | mm |
| STEM ASPECT | Upright | |
| STEM COLOR (and bark color, if applicable) | Near 143A | RHS |
| STEM PUBESCENCE? | Pubescent | |
| OTHER PLANT/STEM CHARACTERISTICS | None | |
| LEAF ARRANGEMENT | Alternate | |
| COMPOUND OR SIMPLE? | Simple | |
| LEAF (LEAFLET) SHAPE | Cordate | |
| LEAF (LEAFLET) TIP | Acute | |
| LEAF (LEAFLET) BASE | Cordate | |
| LEAF LENGTH | About 64.3 | mm |
| LEAF WIDTH | About 72.9 | mm |
| LEAF THICKNESS | About 1.1 | mm |
| LEAF (LEAFLET) TEXTURE | Smooth | |
| LEAF PUBESCENCE? (Upper side) | Smooth, Pubescence sparsely | |
| LEAF PUBESCENCE? (Lower side) | Smooth, Pubescence densely | |
| LEAF PUBESCENCE COLOR | Near NN155C | RHS |
| LEAF (LEAFLET) MARGIN | Palmately lobed, dentate | |
| DEGREE OF SERRATION | Shallow | |
| UNDULATION | Undulated, weak | |
| VENATION PATTERN | Reticulate venation | |
| LEAF COLOR, IMMATURE, UPPER SIDE | Near 137C | RHS |
| LEAF COLOR, IMMATURE, LOWER SIDE | Near 93C | RHS |
| LEAF COLOR, MATURE, UPPER SIDE | Near 137B | RHS |
| LEAF COLOR, MATURE, LOWER SIDE | Near 191A | RHS |
| VENATION COLOR, UPPER SIDE | Near 144A | RHS |
| VENATION COLOR, LOWER SIDE | Near 144A | RHS |
| PETIOLE LENGTH | About 50.0 | mm |
| PETIOLE DIAMETER | About 2.4 | mm |
| PETIOLE TEXTURE | Tomentose | |
| PETIOLE COLOR | Near 144A | RHS |
| WING | Absent | |
| STIPULES, TENDRILS, THORNS, SPINES OR PRICKLES? IF SO, GIVE COLOR AND SIZE | Absent | |
| OTHER FOLIAGE CHARACTERISTICS | None | |
| FILAMENT COLOR | 4D | RHS |
| FILAMENT LENGTH | About 1.2 | mm |
| STYLE LENGTH | About 4.0 | mm |
| STYLE COLOR | 145C | RHS |
| FLOWER ARRANGEMENT | Daisy-type inflorescence borne in upper leaf | |

-continued

PLANT VARIETY DESCRIPTION

| CHARACTERISTIC | APPLICATION VARIETY Sunsenebubakai | |
|---|---|---|
| INFLORESCENCE TYPE OR FORM (if applicable) | Mounding | |
| INFLORESCENCE DIAMETER | About 22.0 | cm |
| INFLORESCENCE HEIGHT | About 26.0 | cm |
| FLOWER TYPE or FORM | Single | |
| FLOWERING HABIT | Continuous flowering Buds grow one after another from axils. | |
| QUANTITY OF FLOWERS and BUDS PER PLANT | About 144 | |
| QUANTITY OF FLOWERS PER INFLORESCENCE | About 6 | |
| NATURAL FLOWERING SEASON | Substantially continuous blooming from winter to late spring in Japan | |
| TIME TO FLOWER OR RESPONSE TIME | About 24 weeks | |
| FRAGRANCE | Absent | |
| FLOWER BUD LENGTH | About 7.3 | mm |
| FLOWER BUD DIAMETER | About 6.3 | mm |
| FLOWER BUD SHAPE | Globose | |
| FLOWER BUD COLOR | Near 144A | RHS |
| FLOWER ASPECT; i.e., UPRIGHT, OUTWARD, DROOPING, etc. | Upright | |
| FLOWER SHAPE | Daisy like shape | |
| FLOWER DIAMETER | About 81.0 | mm |
| FLOWER DEPTH (HEIGHT) | About 12.0 | mm |
| FLOWER LONGEVITY ON PLANT | About 2 weeks at around 15° C. | |
| PERSISTENT OR SELF-CLEANING? | Persistent | |
| *RAY FLORETS | | |
| RAY FLORET TEXTURE, UPPER SURFACE | Velvety | |
| RAY FLORET TEXTURE, LOWER SURFACE | Smooth | |
| RAY FLORET ARRANGEMENT | Daisy type | |
| RAY FLORET NUMBER | About 13 | |
| RAY FLORET SHAPE | Narrow elliptic | |
| RAY FLORET MARGIN | Entire | |
| RAY FLORET TIP | Bitten | |
| RAY FLORET BASE | Acute | |
| RAY FLORET LENGTH | About 31.0 | mm |
| RAY FLORET WIDTH | About 7.9 | mm |
| RAY FLORET COLOR, WHEN OPENING, UPPER SIDE | Near Main N89A Center NN155C | RHS |
| RAY FLORET COLOR, WHEN OPENING, LOWER SIDE | Near Mixed 93B and NN155C, Base NN155C only | RHS |
| RAY FLORET COLOR, FULLY OPENED, UPPER SIDE | Near Main 95B Center NN155C | RHS |
| RAY FLORET COLOR, FULLY OPENED, LOWER SIDE | Near Mixed 94B and NN155C, Base NN155C only | RHS |
| *DISC FLORET | | |
| DISC DIAMETER | About 16.0 | mm |
| DISC COLOR (DISC FLORET IMMATURE, MATURE) | Near N89C | RHS |
| DISC FLORET NUMBER | About 137 | |
| DISC FLORET SHAPE | Tubular | |
| DISC FLORET TIP | 5 pointed | |
| DISC FLORET BASE | Fused | |
| DISC FLORET LENGTH | About 7.2 | mm |
| DISC FLORET DIAMETER | About 1.2 | mm |
| INVOLUCURE SHAPE | Cup shape | |
| INVOLUCURE TEXTURE | Smooth | |
| INVOLUCURE COLOR | Near 143A | RHS |
| INVOLUCURE LENGTH | About 7 | mm |

-continued

PLANT VARIETY DESCRIPTION

| CHARACTERISTIC | APPLICATION VARIETY Sunsenebubakai | |
|---|---|---|
| INVOLUCURE DIAMETER | About 8.4 | mm |
| INVOLUCURE ARRANGEMENT | Single whorl, fused | |
| NUMBER OF INVOLUCURAL BRACTS (PHYLLARIES) | About 15 | |
| INVOLUCURAL BRACT (PHYLLARY) SHAPE | Lanceolate | |
| INVOLUCURAL BRACT (PHYLLARY) MARGIN | Entire | |
| INVOLUCURAL BRACT (PHYLLARY) TIP | Narrow acute | |
| INVOLUCURAL BRACT (PHYLLARY) BASE | Fused | |
| INVOLUCURAL BRACT (PHYLLARY) TEXTURE | Smooth | |
| INVOLUCURAL BRACT (PHYLLARY) LENGTH | About 8.5 | mm |
| INVOLUCURAL BRACT (PHYLLARY) WIDTH | About 2.2 | mm |
| INVOLUCURAL BRACT (PHYLLARY) COLOR, UPPER SIDE | Near 144A | RHS |
| INVOLUCURAL BRACT (PHYLLARY) COLOR, LOWER SIDE | Near 144C | RHS |
| PEDUNCLE LENGTH | About 32.3 | mm |
| PEDUNCLE DIAMETER | About 2.9 | mm |
| PEDUNCLE ANGLE | Upright to semi-upright | |
| PEDUNCLE STRENGTH | Medium | |
| PEDUNCLE TEXTURE | Smooth | |
| PEDUNCLE COLOR | Near 144A | RHS |
| STAMEN NUMBER | 5 per a disc floret | |
| ANTHER SHAPE | Ellipsoidal | |
| ANTHER COLOR | Near N186A | RHS |
| ANTHER LENGTH | About 1.5 | mm |
| AMOUNT OF POLLEN | Medium | |
| POLLEN COLOR | Near 7B | RHS |
| PISTIL LENGTH | About 7.0 | mm |
| PISTIL NUMBER | 1 per a ray and disc floret | |
| STIGMA SHAPE | Bi-parted | |
| STIGMA COLOR | Near N186A | RHS |
| OTHER FLOWER CHARACTERISTICS | None | |
| OVARY COLOR | 145C | RHS |
| QUANTITY OF SEEDS | Seed production has not been observed. | |
| ROOT STRUCTURES such as BULBS, CORMS or RHIZOMES? | Fibrous root | |
| LOW TEMPERATURE TOLERANCE | 0 ° C. (However, the plant would be seriously damaged by frost, as other *Senecio* Plant, at any temperature.) | |
| HIGH TEMPERATURE TOLERANCE | Around 30° C. | |
| DISEASE RESISTANCE AND/OR SUSCEPTIBILITY | Typical for *Senecio* | |
| PEST RESISTANCE AND/OR SUSCEPTIBILITY | Typical of *Senecio* | |

This new variety of *Senecio* plant having the above botanical characteristics is suitable for flower bedding and potting, particularly in hanging pots or planters.

What is claimed:

1. A new and distinct variety of *Senecio* plant named 'Sunsenebubakai', substantially as herein illustrated and described.

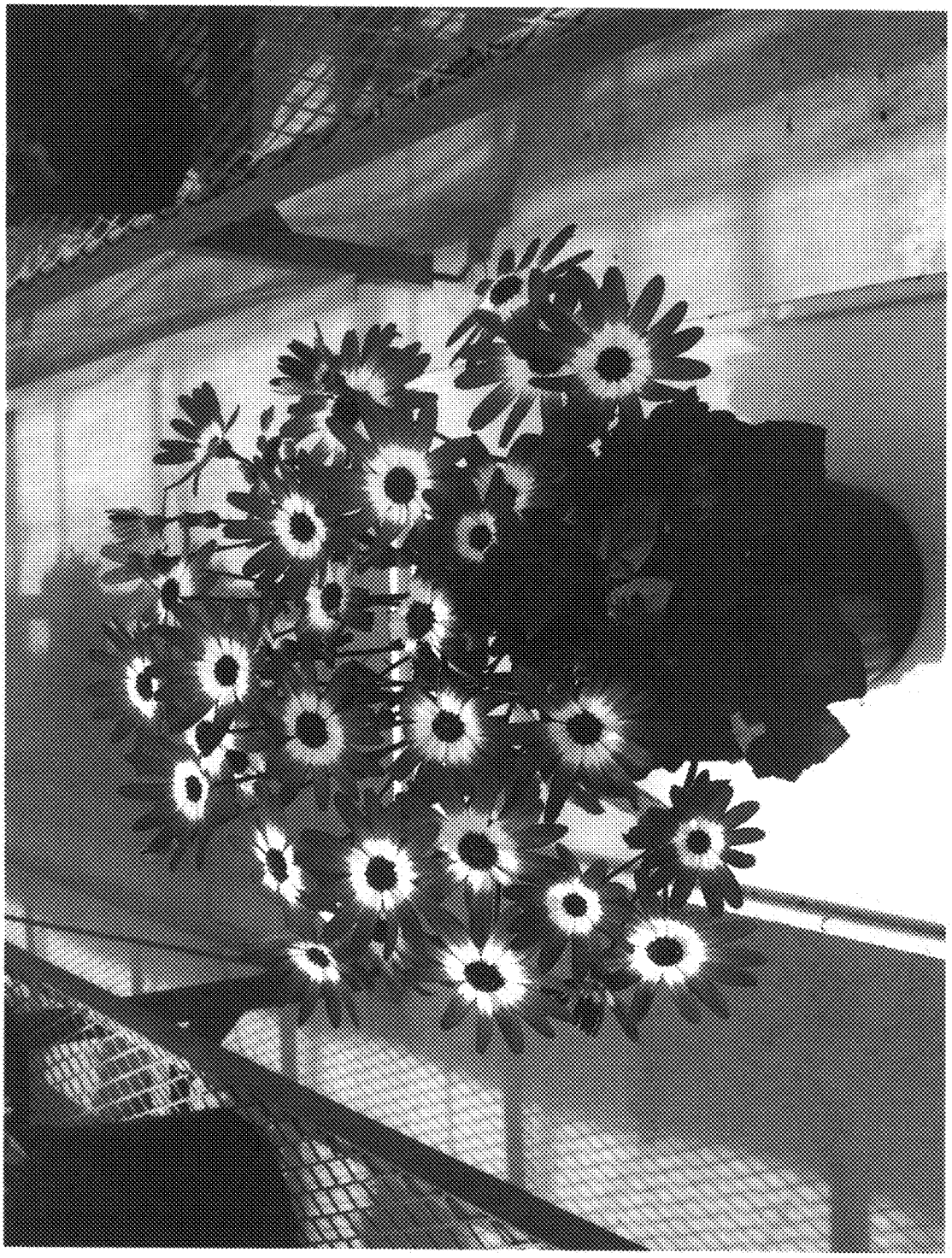

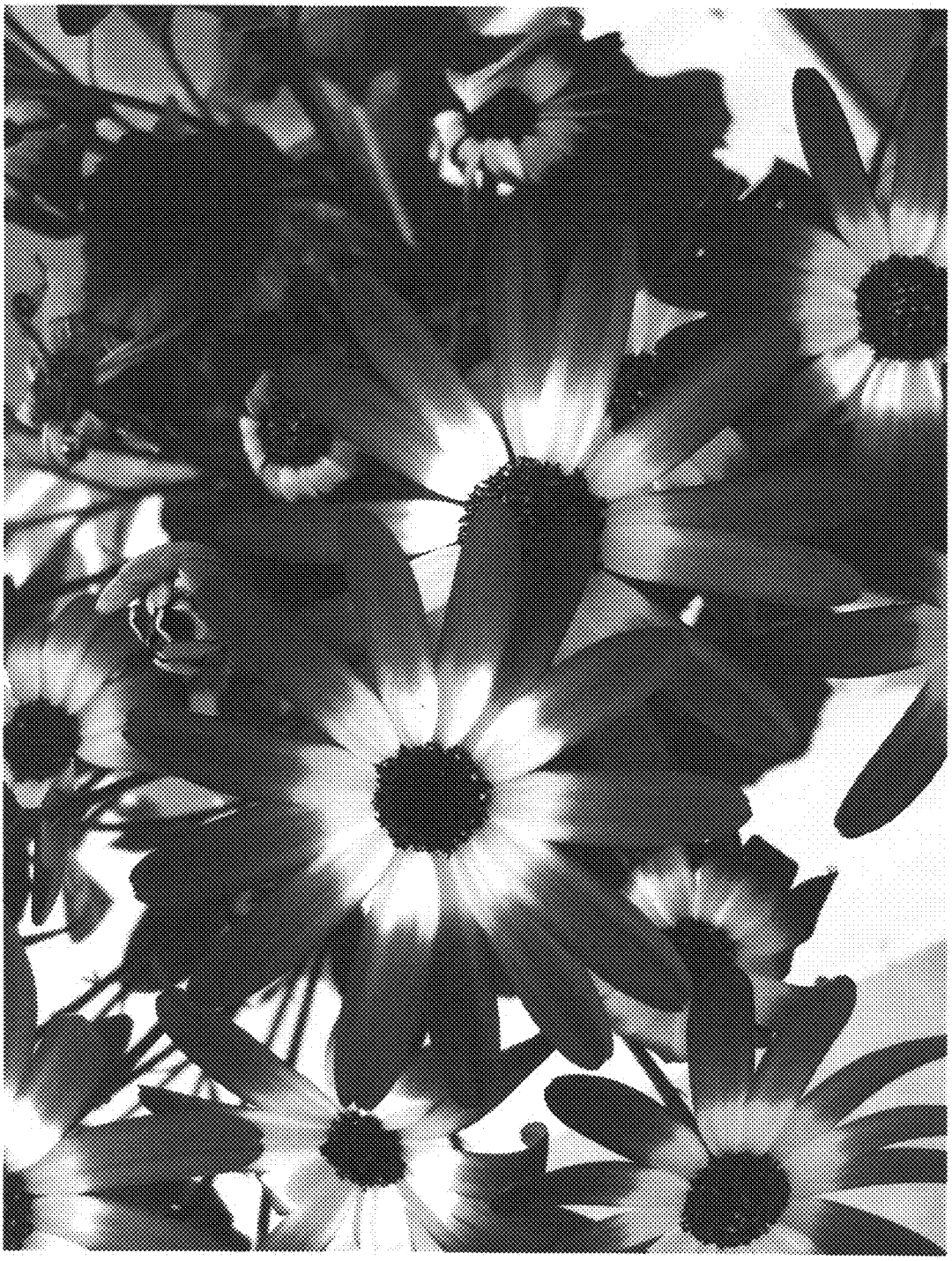

* * * * *